US006309662B1

(12) United States Patent
Buchanan

(10) Patent No.: US 6,309,662 B1
(45) Date of Patent: Oct. 30, 2001

(54) USE OF ANTI-INFLAMMATORY DRUGS FOR TREATMENT OF DERMATOLOGICAL CONDITIONS

(76) Inventor: Janet Buchanan, 362 Roup Ave., Pittsburgh, PA (US) 15232

( * ) Notice: Subject to any disclaimer, the term of this patent is extended or adjusted under 35 U.S.C. 154(b) by 0 days.

(21) Appl. No.: 09/519,831

(22) Filed: Mar. 6, 2000

Related U.S. Application Data

(60) Provisional application No. 60/155,689, filed on Sep. 23, 1999.

(51) Int. Cl.⁷ ..................................... A61F 13/00
(52) U.S. Cl. ........................... 424/435; 514/252
(58) Field of Search ............... 514/252; 424/435

(56) References Cited

U.S. PATENT DOCUMENTS

| 4,868,219 | 9/1989 | Thornfeldt | 514/663 |
|---|---|---|---|
| 4,959,210 | 9/1990 | Smiles et al. | 424/85.7 |
| 5,006,338 | 4/1991 | Luenemann | 424/195.1 |
| 5,217,972 | 6/1993 | Grohe et al. | 514/254 |
| 5,286,754 * | 2/1994 | Streuff et al. | 514/772.3 |
| 5,560,925 | 10/1996 | Sawai et al. | 424/464 |
| 5,834,513 * | 11/1998 | Ptchelintsev et al. | 514/561 |
| 5,847,003 | 12/1998 | Ptchelintsev et al. | 514/532 |
| 5,994,372 * | 11/1999 | Yaksh | 514/327 |
| 6,071,962 * | 6/2000 | Ptchelintsev et al. | 514/558 |

OTHER PUBLICATIONS

Mary W. Chang, et al. "Mucocutaneous Manifestations of the hyper–IgM Immunodeficiency Syndrome", Journal of the American Academy of Dermatology, Feb. 1998, pp. 191–193.

* cited by examiner

*Primary Examiner*—Thurman K. Page
*Assistant Examiner*—Liliana Di Nola-Baron
(74) *Attorney, Agent, or Firm*—Webb Ziesenheim Logsdon Orkin & Hanson, P.C.

(57) ABSTRACT

A method of treating or preventing recurrence of warts including a step of administering to a patient an anti-inflammatory drug, particularly, ciprofloxacin.

1 Claim, No Drawings

USE OF ANTI-INFLAMMATORY DRUGS FOR TREATMENT OF DERMATOLOGICAL CONDITIONS

RELATED APPLICATION

This application claims the benefit of United States Provisional Patent Application Serial No. 60/155,689, filed Sep. 23, 1999.

BACKGROUND OF THE INVENTION

1. Field of the Invention

The present invention relates to the use of anti-inflammatory drugs for generation of a Th-1=IgG2a=CMI response for treatment of dermatological conditions.

2. Prior Art

Dissemination of the human papillomavirus has been found to be associated with suppression of cytokines and other factors leading to an ineffective Th-1 cell-mediated response. The regression of the human papillomavirus has been found to be associated with an increase in the expression of cytokines in a cell-mediated response. as well as a decrease in the viral load, and any markers associated with proliferation and differentiation. It is also recognized that Th-1 cells are involved in the induction of cellular immunity and this is characterized by a lower or absent antibody production. However, some Th-1 responses are associated with strong antibody production of IgG2a, IgG2b, and IgG3 subclasses. When a humoral response with strong antibody production does not develop. there is an incomplete cell-mediated response toward a pathogen. This explains the lack of humoral activities that is seen with the human papillomavirus.

Warts are produced by eruption of the underlying human papillomavirus (HPV). The development of warts is due to direct contact with virus particles. The risk of infection of warts depends not only the virulence of the virus particles, but also on the patient's susceptibility to viral attack and strength of the patient's immune system. Immunodeficient patients have greater susceptibility to infection. inadequate treatment for HPV, and frequent recurrences. Most standard therapies are ablative and caustic and treat only the visibly appearing warts and do not treat the underlying virus.

Certain quinolones have been reported as having some antiviral activity. In particular, ofloxacin, ciprofloxacin. and norfloxacin have been shown to inhibit HIV reverse transcriptase and a class of related quinolones are described in U.S. Pat. No. 5,217,972 as effective in the treatment or prevention of certain human and animal viral diseases. None of those indications however include HPV or warts.

Current treatments for genital warts include podophyllin, other acids, interferons, imiquimod, and other treatment mechanisms such as freezing, frying, cutting, boiling, burning, and topically applying immunomodulating measures to eradicate genital warts. This wide range of essentially destructive therapies and a few nondestructive therapies indicates that none have been found to be outstandingly effective. Most of these therapies have been used for years, and are painful for adults and not tolerated by children. Some can even result in scarring without demonstrating good long-term clinical results. The greater incidence of anogenital warts in the general population includes children. Children have very limited treatment options.

Optimum therapeutic strategy of anogenital infection would be a therapy that accelerates the induction of a strong virus specific immune response to effectuate wart regression with less pain and that could be well-tolerated by adults and children. This would lead to decreased viral persistence, recurrence, and transmission. Viral persistence in the form of visible warts are common and can eventually lead to anogenital neoplasia. The consequences of the lack of optimum therapy results in viral persistence in the form of warts. Warts are not just insignificant lesions, but can in the future lead to malignancies regardless of the immune status of the patient or HPV type. HPV genomes have been found in skin cancers and other types of cancers. Low risk types of HPV do not necessarily mean no risk for malignancies. High risk types of HPV and immunodeficiencies only create a greater predisposition leading to the process of malignant transformation. This phenomena of malignant transformation is frequently seen in immunocompromised patients and in viral persistence of high risk HPV types.

HPV is a systemic rather than just a localized skin manifestation. Untreated or recurrent anogenital warts can be transmitted not only sexually, but from an infected mother to her child. HPV has been found in the amniotic fluid from some pregnant women with cervical lesions. This very early transmission source as well as the presence of warts in the birth canal can lead to the development of life-threatening laryngeal papillomas. These may not develop at birth but can develop anytime during the first few years of a child's life. The median age being 3 years of age. There are also cases of newborns with anoTenitai warts present at birth or developing them in the first few years after birth. Autoinoculation and fomite transmission are other vehicles of non-sexual transmission of the genital human papillomavirus infection.

An optimum strategy for treatment of HPV would be in the form of a systemic immunomodulating medication with associated antiviral properties. It would not only impact a new form of therapy for existing warts, but could demonstrate effectiveness prophylactically. Prophylaxis could contribute immeasurably to less recurrence of warts and less transmission of this virus. Eradication of warts by whatever therapeutic measure that is employed only eliminates the visible presence of the genital papillomavinis, which are warts. It does not eliminate or address the underlying genital papillomavirus which leads to recurrences and transmission of this virus. Recurrences can occur during pregnancy or can be triggered by another virus or infection. States of immunocompromization created by conditions such as pregnancy, illness, stress, or infections are risk factors for wart recurrence. All patients with HPV will be vulnerable to recurrences for the rest of their lives.

Recurrences are even more common in immunodeficiencies. In immunodeficient patients and those with more virulent HPV types, viral persistence is a common occurrence. It is also associated with the frequent development of anogenital neoplasia. Anogenital neoplasia in immunosuppressed women persists, recurs, and extends to adjacent areas of the cervix, vagina, vulva, and anus.

Because of the lack of effective current therapy as well as the many aforementioned consequences of persisting anogenital warts, there is a critical need for the development of an optimum more effective therapy for genital papillomavirus infections.

SUMMARY OF THE INVENTION

The present invention provides a method of treating warts by systemic modulation of dermatological conditions using an anti-inflammatory drug. According to the present invention, the anti-inflammatory drug, in particular, ciprofloxacin is administered perorally to a patient suffering from warts or prophylactically to a patient susceptible to recurring warts. The anti-inflammatory drug is believed to stimulate a response which causes the warts to regress.

DETAILED DESCRIPTION OF THE PREFERRED EMBODIMENT

Pathogens, such as HPV, circumvent the early immune system response through various mechanisms so that early detection is avoided. This early resistance to the development of a natural immune response toward the human papillomavirus ensures life-long persistence of the virus in the cells. In the absence of an early generation of an immune response. protection, curative antibody cannot be made.

It is only after whatever therapeutic measures are applied that the inaccessible viron antigen is exposed to the immune system. The viron antigens are biochemical determinants that are not seen prior to therapeutic measures. Once these are seen by the immune system, a response is generated. Antigen presentation leads to the production of IL-12 by macrophages and to the development of a Th-1 response. The Th-1 response leads to a normal or increased production of IL-2, IFN-y gamma, and other factors leading to a strong cell-mediated response involving further activation of macrophages, NK (natural killer) cells, neutrophils, delayed types hypersensitivity (DTH) and the production of IgG2a by B cells, an antibody subclass important in phagocyte-mediated immunity. The effective generation of this response is solely dependent upon the patient's immune system and health status. The importance of the patient being able to develop this response is more significant than any therapeutic measure directly applied to the warts.[1-16] This response has been found to occur not only after direct treatment to the warts, but without treatment in cases of natural regression. Evidence supporting the association of HPV regression with the development of the Th-1 response comes from studies of cytokine expression in regressing and noregressing warts.[1-10] Evidence from both human and animal studies suggest that HPV regression is associated with the development of the Th-1 response after direct treatment or in natural wart regression.[1-11] The key cytokine is IL-12, a regulatory molecule that promotes the differentiation of Th precursers into Th-1 cells.[2,12] IL-12 is produced mainly by macrophages in response to bacteria and intracellular parasites leading to the development of the Th-1 response in response to these microorganisms.[1,12] Recent studies of the papillomavirus have shown that in regressing genital warts, but not in non-regressing warts, the messenger RNA for the p40 chain of IL-12 is consistently present. When regression occurs, it is characterized by infiltrating T cells, and the regressing keratinocytes express bioactive IL-12.[1] The intriguing finding of the association of this regulatory molecule leading to the development of the Th-1 response that was not only found in response to bacteria, intracellular parasites but in wart regression demonstrates the necessity of this response for infectious diseases. Optimum strategy for wart regression would be the capacity of and therapeutic measure to systemically generate this response. Inmmunostimulating, immnunomodulating therapeutic measures are a necessity, but all patients would ultimately benefit from this form of therapy. This type of therapy would not be just another therapy for eradication of warts, but directed to effectuating the immune system's response toward the underlying virus.

According to the present invention, delivery of an anti-inflammatory drug, such as ciprofloxacin hydrochloride, is found to activate the Th-1 response which then leads to production of IgG2a and the development of phagocytic-dependent cell-mediated immunity.

By way of example, ciprofloxacin hydrochloride is an anti-inflammatory drug which is conventionally used for treatment of bacterial infections, such as bronchitis. Ciprofloxacin hydrochloride is sold under the trademark CIPRO® by Bayer Corporation of West Haven, Conn.

Bacterial infections require the development of an effective Th-1 response. Ciprofloxacin hydrochloride up regulates certain cytokines and other factors necessary for the development of a Th-1 response that is required for bacterial clearance as well as HPV regression.

According to the method of the present invention, an anti-inflammatory drug such as ciprofloxacin hydrochloride is administered to a patient suffering from a viral dermatological disorder, such as warts. Unlike prior treatment protocols. the dermatological disorder is not treated with a topical medicament but instead with a perorally delivered drug. When the dermatological disorder being treated is warts. ciprofloxacin hydrochloride is a preferred drug and is preferably delivered twice per day in 500 milligram doses.

Other dosaging rates are also contemplated by the present invention. Dosaging is determined by the amount of drug necessary to cause regression of the viral activity responsible for the dermatological disorder.

It is believed that ciprofloxacin hydrochloride stimulates warts to regress and can be used to prevent recurrence of warts. Hence the present invention is useful both as a method of treating a dermatological disorder and preventing recurrence of the same.

It will be readily appreciated by those skilled in the art that modifications may be made to the invention without departing from the concepts disclosed in the foregoing description. Such modifications are to be considered as included within the following claims unless the claims, by their language, expressly state otherwise. Accordingly, the particular embodiments described in detail herein are illustrative only and are not limiting to the scope of the invention which is to be given the full breadth of the appended claims and any and all equivalents thereof.

1. Stanley M. The immunology of a genital papilloma virus infection. Eur J Dermatol 1998;8:8–12.
2. Majewski S, Jablonska S. Immunology of HPV infections and HPV associated tumors. Int J Dermatol 1998;37:81–95.
3. Frazer, I H. The role of the immune system in anogenital human papillomavirus. Austr J Dermatol 1998;39(Suppl.):S5–S7.
4. Arany I., Tyring S. Status of local cellular immunity in interferon responsive and nonresponsive Human papillomavirus-associated lesions. Sex Transm Dis 1996;November–December:475–479.
5. Farenczy A, Masaru M, Mitao, MD, et al. Latent papillomavirus and recurring genital warts. N Engl J Med 1985;313:784–788.
6. Coleman N, Birley H D L, Renton A M, et al. Immunological events in regressing genital warts. Am J Clin Pathol 1994;102:768–774.
7. Alba S, Rokugo M, Tagami H. Immunohistologic analysis of the phenomenon of spontaneous regression of numerous flat warts. Cancer 1986;58:1246–1251.
8. Gibbs N F. Anogenital papillomavirus infections in children. Curr Opin Pediatr 1998:10(4):393–7.
9. Stantella P, Frega A, Ciccarone M, et al. HPV and intraepithelial neoplasia recurrent lesions of the lower genital tract: assessment of the immune system. Eur J Gynaec Oncol 1998:5:466–468.

10. Cohen B A, Honig P, Androphy E. Anogenital warts in children. Arch Dermatol 1990;126:1575–1580.
11. Ogilvie M M. Serological studies with human papova (wart) virus. J. Hyg Comb 1970;68:479–489.
12. Long K Z, Santos JI. Vitamins and the regulation of the immune response. Pediatr Inf Dis J 1999;10(3):283–288.
13. Siegfried E C, Frasier L D. Anogential warts in children. Advances in Dermatol Mosby-1997;12:141–165.
14. Obalek S, Jablonska S, Favre M, et al. Condyloma acuminata in children: Frequent association with human papillomaviruses responsible for cutaneous warts. J Am Acad Dermatol 1990;23:205–213.
15. Beutner K R. Reitano M V, Richwald G A, et al. External genital warts: Report of the American Medical Association concensus conference. Clin Inf Dis J 1998;27:796–806.
16. Barnett N. Hailen M. Winkelstein J A. Extensive verrucosis in primary immunodeficiency diseases. Arch Dermatol 1983;119:5–7.

I claim:

1. A method of perorally treating warts caused by the papillomavirus in humans wherein ciprofloxacin hydrochloride is administered at a dosage of about 500 milligrams perorally twice per day.

* * * * *

UNITED STATES PATENT AND TRADEMARK OFFICE
CERTIFICATE OF CORRECTION

PATENT NO. : 6,309,662 B1
DATED : October 30, 2001
INVENTOR(S) : Janet Buchanan

It is certified that error appears in the above-identified patent and that said Letters Patent is hereby corrected as shown below:

Column 1,
Line 22, "response. as well" should read -- response, as well --.
Line 30, "does not develop." should read -- does not develop, --.
Line 40, "infection. inadequate" should read -- infection, inadequate --.
Line 45, "ciprofloxacin. and" should read -- ciprofloxacin, and --.

Column 2,
Line 27, "anoTenitai" should read -- anogenital --.

Column 3,
Line 14, "response. protection" should read -- response, protection --.
Line 43, "Th-1 cells.$^{2,12}$" should read -- Th-1 cells.$^{1,12}$ --.

Column 4,
Lines 16-17, "protocols. the" should read -- protocols, the --.

Signed and Sealed this

Nineteenth Day of March, 2002

JAMES E. ROGAN
*Director of the United States Patent and Trademark Office*